United States Patent
Gilleland et al.

(12)

(10) Patent No.: US 6,375,981 B1
(45) Date of Patent: *Apr. 23, 2002

(54) MODIFIED STARCH AS A REPLACEMENT FOR GELATIN IN SOFT GEL FILMS AND CAPSULES

(75) Inventors: Gregory M. Gilleland; Judy L. Turner; Penelope A. Patton; Michael D. Harrison, all of Decatur, IL (US)

(73) Assignee: A. E. Staley Manufacturing Co., Decatur, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/584,413

(22) Filed: Jun. 1, 2000

(51) Int. Cl.$^7$ ............................. A61K 9/48; A61K 9/70; A61K 47/00

(52) U.S. Cl. .................. 424/452; 424/451; 424/484; 424/485; 424/488; 514/778; 514/779; 514/780; 514/782; 514/783; 514/962

(58) Field of Search ................. 424/451, 452, 424/484, 485, 488, 682, 722, 195.1, 195.17, 195.18, 750, 773; 514/778, 779, 780, 782, 783, 962

(56) References Cited

U.S. PATENT DOCUMENTS

| | | | |
|---|---|---|---|
| 3,499,962 A | 3/1970 | Wurzburg et al. ............ 424/35 |
| 3,865,603 A | 2/1975 | Szymanski et al. ......... 106/130 |
| 3,956,173 A | 5/1976 | Towle ......................... 252/316 |
| 4,009,291 A | * 2/1977 | Mitchell et al. ............. 426/548 |
| 4,026,986 A | 5/1977 | Christen et al. ............. 264/301 |
| 4,795,642 A | 1/1989 | Cohen et al. ................ 424/455 |
| 4,804,542 A | 2/1989 | Fischer et al. ............... 424/456 |
| 4,935,243 A | 6/1990 | Borkan et al. ............... 424/441 |
| 5,089,307 A | 2/1992 | Ninomiya et al. .......... 428/35.2 |
| 5,334,640 A | 8/1994 | Desai et al. .................... 524/56 |
| 5,342,626 A | 8/1994 | Winston, Jr. et al. ....... 424/461 |
| 5,393,054 A | 2/1995 | Rouffer ......................... 273/58 |
| 5,451,673 A | 9/1995 | Fishman et al. ............. 536/123 |
| 5,484,598 A | 1/1996 | Schurig et al. .............. 424/401 |
| 5,550,178 A | 8/1996 | Desai et al. .................... 524/56 |
| 5,554,385 A | 9/1996 | Stroud ......................... 424/456 |
| 5,620,757 A | 4/1997 | Ninomiya et al. .......... 428/34.8 |
| 5,726,008 A | 3/1998 | Maskasky ................... 430/569 |
| 5,756,123 A | 5/1998 | Yamamoto et al. ......... 424/451 |
| 5,817,323 A | 10/1998 | Hutchinson et al. ........ 424/439 |
| 5,932,639 A | 8/1999 | Eden et al. ..................... 524/48 |
| 5,976,586 A | 11/1999 | Feller .......................... 426/89 |
| 6,210,709 B1 | 4/2001 | Laba et al. ................. 424/451 |

FOREIGN PATENT DOCUMENTS

| | | |
|---|---|---|
| EP | 0 471 558 A2 | 2/1992 |
| EP | 0 400 484 B1 | 1/1994 |
| EP | 0 409 781 B1 | 6/1994 |
| EP | 0 547 551 B1 | 11/1997 |
| EP | 0 633 896 B1 | 6/1998 |
| WO | WO94/25493 | 11/1994 |
| WO | WO00/10538 | 3/2000 |
| WO | WO01/03677 | 1/2001 |

OTHER PUBLICATIONS

Krochta et al., "Edible and Biodegradable Polymer Films: Challenges and Opportunities," *Food Technology* 51:61–74 (1997).
Lourdin et al., "Influence of Amylose Content on Starch Films and Foams," *Carbohydrate Polymers* 27:261–270 (1995).
Kester et al., "Edible Films and Coatings: A Review," *Food Technology* 40:47–59 (1986).
Shih, "Effects of Additives on the Development of Edible Films," *Chemistry of Novel Foods*, Chapter 14, 1995 International Chemical Congress of Pacific Basin Societies, Honolulu, Hawaii (Dec. 17–22, 1995).
Bergthaller et al., "Potato Starch Technology," *Starch/Stärke* 51:235–242 (1999).
BeMiller et al., "Carbohydrates," *Food Chemistry*, pp. 205–223 (No Date).
"The Birth of a Paintball," *R.P. Scherer Paintballs—How Paintballs are...*, pp. 1–2 (1998).
Picullel, "Gelling Carrageenans,"*Food Polysaccharides and Their Applications*, pp. 205, 210–212, 233–234 (1995).
Rochas et al., "Relation Between the Molecular Structure and Mechanical Properties of Carrageenan Gels," *Carbohydrate Polymers* 10:115–127 (1989).
Hermansson et al., "Effects of Potassium, Sodium and Calcium on the Microstructure and Rheological Behaviour of Kappa–Carrageenan Gels," *Carbohydrate Polymers* 16:297–320 (1991).
Arvanitoyannis et al., "Edible Films Made from Hydroxypropyl Starch and Gelatin and Plasticized by Polyols and Water," *Carbohydrate Polymers* 36:105–119 (1998).
Derwent Abstract WO 9923118 A1.
Derwent Abstract JP 5148388 A.
Derwent Abstract WO 9304670 A.
Derwent Abstract JP 5004914 A.
Derwent Abstract WO 9218014 A.
Derwent Abstract WO 9206672 A.
Derwent Abstract EP 471558 A.
Derwent Abstract WO 9200731 A.
Derwent Abstract EP 400484 A.
Derwent Abstract JP 63170310 A.
Derwent Abstract EP 273823 A.
Derwent Abstract JP 61009258 A.
Derwent Abstract JP 60037966 A.
Derwent Abstract JP 72023384 B.
U.S. Patent Application Ser. No. 09/585,846, filed Jun. 1, 2000.

* cited by examiner

*Primary Examiner*—Jose G. Dees
*Assistant Examiner*—Frank Choi
(74) *Attorney, Agent, or Firm*—Williams, Morgan & Amerson, P.C.

(57) ABSTRACT

Film-forming compositions are disclosed that can comprise, on a dry solids basis, 25 to 75 percent by weight of certain starch derivatives having a DE less than about 1, 25 to 75% plasticizer, and 0.1 to 15% hydrocolloid gum. The starch derviatives can be chemically modified starches which range in molecular weight from 100,000 to 2,000,000. These starch-based systems can completely replace gelatin in edible film-forming applications such as soft and hard gel capsules.

21 Claims, 2 Drawing Sheets

MODIFIED STARCH AS A REPLACEMENT FOR GELATIN IN SOFT GEL FILMS AND CAPSULES

BACKGROUND OF THE INVENTION

This invention relates to starch compositions useful in forming flexible films. More particularly, it relates to film-forming compositions containing certain modified starches.

Gelatin is a protein that forms thermo-reversible films. Gel masses composed of gelatin and a plasticizer such as glycerin are formulated to be liquid above room temperature, form a film when cast on a cooled surface, and re-melt when exposed to higher temperatures again. This ability to re-tackify enables encapsulation of liquid materials in gelatin soft capsules. Films formed from plasticized gelatin set very quickly and have high wet film strength. They are also very elastic with good clarity. Plasticized gelatin also has a relatively low viscosity, even when used at high solids concentrations. In addition, when gelatin is in the presence of water at room temperature, it swells but does not go into solution until heat is applied.

In the manufacture of soft gel films and capsules, the soft gel composition must possess the properties of good wet and dry film strength, insolubility in cold water, oil, and alcohol, solubility in hot water, temperature and pressure sealability, film clarity, film flexibility, edibility, inertness to drugs or other materials to be encapsulated, and rapid setting from a hot liquid to form a gel. In the manufacture of photographic elements, the soft gel films must possess the qualities of clarity, strength, setting power, flexibility, and non-interaction with other chemicals in the photographic film.

Although gelatin is useful in soft gel applications because of its rapid gelling ability, excellent film forming properties, and ability to impart oxygen impermeability, it has the disadvantages of high cost, limited availability, non-kosher status for food products and, at times, batch property variations. Because of these shortcomings, those industries where the need for gelatin is greatest have long sought means for replacing gelatin.

A useful gelatin replacer must be compatible with common plasticizers and fill materials used in the industry, and must provide properties equivalent to those of the gelatin which it is replacing for a particular application, e.g., film or binding strength in the pharmaceutical industry, phototransmissibility and resistance to abrasion in the photographic industry, and binding strength in the adhesive industry.

SUMMARY OF THE INVENTION

One aspect of the present invention is a film-forming composition that comprises starch material selected from the group consisting of modified starch and waxy starch; gum; and plasticizer. The modified starch or waxy starch has a dextrose equivalent (DE) of less than about 1, and preferably has no measurable DE. This composition can be, but is not required to be, 100% gelatin-free. Thus, the composition can be used as a gelatin replacement, or as an extender in gelatin formulations.

The composition typically will be prepared with water, and have a solids concentration of about 30–70% by weight. The solids in the composition preferably comprise 25–75% starch material, 25–75% plasticizer, and 0.1–15% gum. In certain preferred embodiments of the invention, the weight ratio of gum to starch is from about 0.1:1 to about 1:1, and the weight ratio of starch and gum to plasticizer is from about 1:0.8 to about 1:3.

The starch material preferably comprises starch which has been chemically modified with a monoreactive moiety to a degree of substitution of least about 0.015. It is also preferred that the starch material has an average molecular weight between about 100,000–2,000,000. In a particularly preferred embodiment, the starch material is selected from the group consisting of ether and ester derivatives of starch, such as hydroxypropyl, hydroxyethyl, succinate, and octenyl succinate starch. One specific embodiment of the invention comprises hydroxypropylated potato starch having a degree of substitution of about 0.015–0.30 and a molecular weight of about 100,000–2,000,000.

The gum preferably is selected from the group consisting of carrageenan, locust bean, xanthan, gellan, agar, alginates, guar, gum arabic, and pectin. A combination of kappa carrageenan and iota carrageenan, most preferably in a weight ratio of about 1:1, is especially preferred. The plasticizer preferably comprises at least one polyol, such as glycerol, sorbitol, maltitol, or a mixture of one or more of these. The composition of the present invention can optionally also comprise at least one monovalent or divalent cation, such as sodium, potassium, and calcium salts, or mixtures thereof.

Another aspect of the invention is an edible film that comprises the above-described starch-based composition, usually with much of the water removed. Yet another aspect of the invention is a soft gel capsule that comprises a sealed capsule wall and a first substance that is encapsulated by the sealed capsule wall. The capsule wall comprises the above-described starch-based composition. In one embodiment of the invention, the film or the capsule wall consists essentially of the combination of starch material, gum, and plasticizer.

The first substance encapsulated by the capsule wall can be any of a variety of materials which have been encapsulated by gelatin in the past. Many such substances are edible, including drugs, vitamins, nutritional supplements, and pre-measured food ingredients such as flavorings. It can also comprise, for example, photographic or dye solutions.

Another aspect of the invention is a method of encapsulating a first substance. This method comprises the steps of: providing a first substance and an edible film as described above; and encapsulating the first substance in the film. Preferably, the film used in this method has been formed on a surface having a temperature of at least about 100° F.

One object of this invention to provide an economical means for replacing gelatin in compositions utilized in the production of soft gel for food, pharmaceutical, and industrial applications. It is a further object of this invention to provide starch-based materials which are compatible with the existing application equipment used for manufacture of the various products which are primarily comprised of gelatin films.

The starch-based systems of the present invention, when incorporated as a replacement for gelatin in aqueous solutions, display properties superior to those of their parent base starch. More precisely, modified starches that have been chemically modified with monoreactive moieties to a degree of substitution of at least 0.015 DS, and degraded to molecular weights between 100,000 and 2,000,000, or, alternatively, waxy starches, when combined with gum and plasticizing agents, are a highly functional replacement for gelatin in soft gel film forming applications. The presence of gum increases the rate of film formation and enhances film strength.

In compositions of the present invention, the starch and gum preferably are mixed with plasticizers at ratios ranging from about 1 part starch and gum to about 0.8–3 parts plasticizer. The total solids in the composition preferably range from about 30 to 70% weight. Edible films are prepared by blending together the starch, gum, plasticizer, and water, and heating the mixture to a temperature and for a time sufficient to gelatinize the starch fully, (e.g., 80–100° C. for 10–60 min). A vacuum can be used either during or after cooking to remove entrained air and improve film properties. Additional materials may be added to the mixture of starch and plasticizer in order to impart improved functionality. Furthermore, properties of this system can be modified by the inclusion of various mono and divalent cations, including but not limited to sodium, potassium, and calcium. The mixture is then sheeted, while hot, to form a thin film. This film can be formed into soft gel capsules, encapsulating pharmaceutical, nutritional, photographic, or other materials, using well-known techniques.

The modified starch-based compositions of the present invention provide an acceptable balance of critical variables including mass viscosity and pot life, film rate, wet film strength, dry film strength and flexibility, and thermoreversibility.

In one embodiment of the invention, wet film strength is significantly improved by increasing the temperature of the surface on which the film is formed. It is preferred in the present invention to use film-forming surface temperatures of about 100° F. or greater. Commercial capsule filming drum temperatures are often set around 50° F. for gelatin filming, but can easily be adjusted to 100–110° F. Breaking strengths can be increased by as much as 500% by increasing surface temperature from 53° F. to 150° F. Films cast at 105° F. can have as much as twice the breaking strength films cast on 53° F. surfaces.

In one particularly preferred embodiment, the gum component of the composition consists essentially of 50% kappa carrageenan and 50% iota carrageenan. This combination can increase film strength by as much as 50% over films formed with 100% kappa carrageenan as the gum component, increase film elasticity, reduce the viscosity of the hot mass, lower the minimum temperature at which the gelled mass can be handled in liquid form, and lower the gel-setting temperature of the mass. This composition also broadens the temperature range over which the mass gels, which can improve the ease of film sealing.

The present invention has a number of benefits. One advantage of the invention is that it is a simple, cost-effective, dependable, intrinsically safe, Kosher, and efficient means for replacing the gelatin used in soft gel capsule compositions.

Another advantage of the invention is that the preparation of the starch-based compositions can be carried out by ordinary means with conventional manufacturing apparatus. The resulting compositions can be utilized in any commercial process requiring gelatin and to which conventional coating and drying methods are adaptable. Examples of end-product uses for the compositions of the present invention include encapsulated bath beads, paint balls, and pharmaceuticals. Therefore, the present invention provides a novel, efficient means for replacing gelatin in these and other applications.

DETAILED DESCRIPTION OF SPECIFIC EMBODIMENTS

Figure 1:
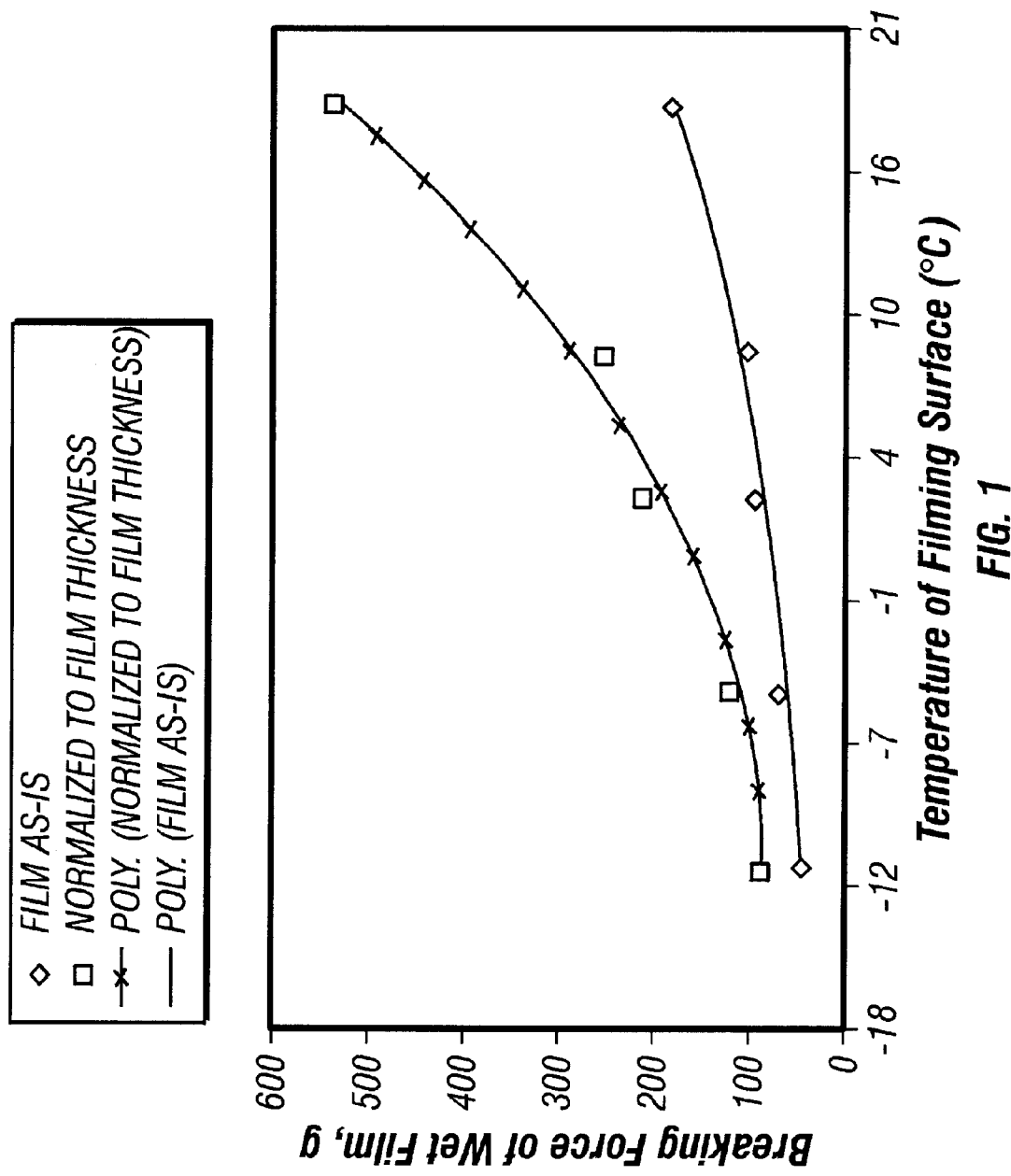
FIG. 1 is a graph showing the effect of the temperature of the surface on which a film is formed on the strength of that film.

Examples of modified starches that can be used in the present invention include non-retrograding starches derived by chemical modification of starch from any plant source, including corn, waxy maize, potato, sweet potato, wheat, rice, sago, tapioca, sorghum, high amylose corn, and the like. The particular starch chosen will depend on its performance, availability, and cost. The starch should have a DE less than about 1, and preferably has no measurable DE (using the Lane-Eynon method). Among the useful modified starches are the common ether and ester derivatives of starch, including but not limited to hydroxypropyl, hydroxyethyl, succinate, and octenyl succinate starch derivatives. Also included among the modified starches suitable for use in the practice of this invention are the thermally converted, fluidity or thin boiling type products derived from the aforementioned types of chemically modified starches. Such materials may be of lower molecular weight, prepared by heating the modified starch alone or by subjecting the starch to a hydrolytic acid and/or heat treatment, or by any other known method designed for the thermal conversion of the starch, such as enzymic heat treatment.

Preferred modified starches are the hydroxypropyl derivatives of potato starch having a degree of substitution from 0.015–0.30 ds and a molecular weight of from 100,000 to 2,000,000. In the case of waxy starches of corn, potato, etc., the branches of the amylopectin replace the function of the ether or ester substituents; these starches are functional in the present invention without additional chemical modification, although their properties are not impaired by additional modification, and are enhanced by molecular weight reduction.

Suitable plasticizers include, but are not limited to, glycerol, sorbitol, and maltitol. Suitable hydrocolloid gums include carrageenan, locust bean gum, xanthan gum, gellan gum, agar, alginates, guar gum, gum arabic, and pectin.

The properties of the composition can be enhanced by the addition of certain cations, including but not limited to sodium, potassium, and calcium. The presence of these cations, in combination with certain gums, generally enhances viscoelastic properties and gel strength.

A variety of optional ingredients may be incorporated into the starch compositions of this invention, before, during, or after cooking the starch. Among the suitable additives which may be utilized are preservatives, colorants, flavoring agents, hardeners, antifoggers, sensitizers, and spreading agents. The inclusion of such additives has no adverse effect upon the properties exhibited by the novel starch-based compositions of the present invention.

A composition of the present invention is formed by combining the dry solids (i.e., the modified starch or waxy starch, gum, and plasticizer, plus any other additives), slurrying in water, and heating at a temperature and for a time sufficient to gelatinize the starch. Optionally, this can take place under a vacuum. Films can be formed from these starch-based compositions by any conventional method designed to solubilize and deposit a continuous coating or layer of the solution onto a substrate or mold of any form. Among the suitable coating techniques are spraying, dipping, air knife, trailing blade, reverse and direct roll coaters, etc. A film, such as an overcoating or capsule shell, may then be formed by drying the coated solution to a desired moisture content, using any means suitable for the particular purpose. Suitable conventional means include warm or cold air impingement, low humidity chamber or oven drying, etc. For example, in the pharmaceutical industry, soft gel capsules are prepared by casting a film of the gelatin solution and then continuously passing two ribbons of the film between two opposing rollers, each of which is equipped with an internal vacuum that draws in the film through half capsule wells engraved in its surface. The capsule contents are deposited between the shell halves as they are formed and sealed. The process is continuous, ending with the filled capsules being automatically conveyed to and through a drying unit that partially dries the capsule. Drying is completed in warm air tunnels.

The films of the present invention can be re-melted, and two or more of these re-melted films can be joined to form a seal.

The invention is particularly efficacious in the soft gel capsule manufacturing process that calls for film-forming materials, but it is not limited thereto. The characteristics exhibited by the present, novel starch formulations, particularly their ability to serve as a total replacement for gelatin, permit them to be used in a wide range of applications.

Although the emphasis has been placed on describing this invention in connection with film-forming gelatin-free compositions, compositions of the present invention can also be utilized as extenders in gelatin compositions such as creams, emulsions, binders, adhesives, etc. Further compositions of the present invention can be used in the replacement of gelatin in hard shell capsule manufacturing.

EXAMPLES

The invention will be further illustrated by, but is not intended to be limited to, the following examples.

Compositions were prepared containing the component amounts given in Examples 1–7 on a dry solids basis. Starch molecular weights were measured by gel permeation chromatography and weight averaged. In Examples 1–7, the starch, plasticizer, and gum, if used, were mixed with sufficient deionized water (except where indicated) to give a total slurry mass of 35 g. The components were mixed together in the cup of a Rapid Visco Analyzer (Model RVA-4D, Foss Food Technology, Eden Prairie, Minn.) (hereafter referred to as "RVA"), and heated, using 160 rpm stirring, to 98° C. over 4.5 minutes. The mixture was held at 98° C., with continued stirring, for 6.5 minutes, then transferred to a chilled surface and drawn into a film of 0.5 mm thickness for film testing. A second paste of the same composition was cooked in the same way and then transferred into a pre-heated glass jar, tightly capped, and placed into an oven for pot life evaluations.

In particular, in Examples 1–7, the film samples were prepared by casting a layer of the test solution at about 1 80° F. (82° C.) onto a Teflon-coated piece of glass (approximately 9 in×13 in). The bottom of the glass was in contact with circulating cold water so that the surface temperature of the glass was 52° C. The film was formed by pouring the hot paste onto the Teflon surface and then quickly drawing the paste across the glass using a Bird Applicator or similar device, the gap width of which could be adjusted to control film thickness. Wet film thicknesses were typically 0.5–0.8 mm. The films were cast, dried, and aged in a room controlled to 70° F. and 25–30% relative humidity.

The viscosity of the starch mixture was measured by the RVA instrument, which records viscosity throughout the cook.

Pot life was evaluated by transferring the hot paste into preheated glass jars with screw lids, and placing these in a 180° F. oven. The fluidity of the mass was evaluated after 2 hours by tipping the jars upside down and assigning a flow rating of 0–5. A mass that flowed with the ease of water was given a rating of 5; a mass which did not flow at all was given a rating of 0. The oven temperature was then lowered by 10° C. and the samples allowed to equilibrate for 2 hours, and then their flow properties re-assessed. The oven was lowered in 10° F. increments until all samples had a flow rating of zero—that is, they had all gelled.

Thermo-reversibility was assessed by reheating the pot life samples, described above, in 10° F. increments, allowing them to equilibrate at each temperature, and then assigning a flow rating using the same criteria as for pot life.

The films were evaluated for rate of filming using a Gardco Electronic Multicycle Circular Drying Time Recorder, and following test method procedure ASTM D 5895. The recorder was placed above the wet film, and a stylus was lowered onto the surface of the film and allowed to rotate for a defined time of 10 minutes. Three points were determined from this test: tack free, dry hard, and dry through. Tack free is defined as the point in the path made by the stylus on the film where the continuous track ends and a discontinuous track or tear begins. Dry hard is the point in the path where the stylus no longer tears the film, and only leaves a visible trace. Dry through is reached when the stylus no longer leaves any visible track on the film.

The tensile strength of the wet film was measured using a Stable Microsystems TA-XT2 Texture Analyzer. To do this, 0.5 in×8 in strips were cut from the wet film 5 minutes after it was cast and these were loaded onto the Texture Analyzer. The tensile test was started 15 minutes after the film was cast.

Film appearance (color and clarity) was evaluated on the basis of visual observation.

Example 1

5.2 g potato starch, substituted with 3 wt % hydroxypropyl groups and of 600,000 molecular weight 0.75 g kappa carrageenan 9.7 g Sorbitol Special (obtained from SPI Polyols, New Castle, Del.)

Example 2

8.4 g potato starch, substituted with 0.5% hydroxypropyl groups and of 600,000 molecular weight 11.8 g Sorbitol Special

Example 3

8.4 g potato starch, substituted with 3.0% hydroxypropyl groups and of 600,000 molecular weight 11.8 g Sorbitol Special 0.5 mm thickness.

Example 4

5.2 g potato starch, substituted with 3 wt % hydroxypropyl groups and of 600,000 molecular weight 0.75 g gellan 9.7 g sorbitol 0.5 mm thickness.

Example 5

5.2 g waxy corn starch of 800,000 molecular weight
0.75 g kappa carrageenan
9.7 g sorbitol

Example 6

5.2 g potato starch, substituted with 3 wt % hydroxypropyl groups and of 600,000 molecular weight
0.75 g kappa carrageenan
9.7 g glycerine

Example 7

5.2 g potato starch, substituted with 3 wt % hydroxypropyl groups and of 600,000 molecular weight
0.75 g kappa carrageenan
9.7 g Sorbitol Special
Sufficient 1% NaCl to bring to 35 g total mass.

The physical properties of the hot starch/plasticizer pastes for Examples 1–7, and the resulting films, are listed below in Table 1.

ferred to preheated glass vials and placed in a 1 80° F. oven. After 2 hours equilibration, the vials were tipped and the flow of the mass observed, and a ranking assigned and recorded. The oven temperature was then reduced by 10° F. and the samples allowed to equilibrate for an additional 2 hours. The "minimum flow temperature" was defined as the lowest temperature at which the mass would easily flow in the vial. It was viscous but "pourable". The "gel temperature" was the highest temperature at which the mass did not flow at all. Since the samples were evaluated in 10° F. increments, the temperature assignments are approximate.

The kappa carrageenan used for this experiment was SKW Satiagel RPT 8/60 Kappa Carrageenan. The iota carrageenan used was FMC SD 389 PF Iota Carrageenan.

During conventional production of gelatin soft-gel capsules, the hot gelatin mass is cast onto a cooled drum (50–55° F.). In this experiment, the surface onto which the mass was cast was heated by the circulating water stream, in order to slow the rate of cooling of the composition. FIG. 1 shows the variation in wet strength of the films formed as the surface temperature varied.

Increasing the temperature of the filming surface dramatically increased wet film strength. (Wet film strength is the important strength parameter since the film must have sufficient integrity within 1–4 minutes of casting to survive

TABLE 1

| Example number | Peak viscosity during cook, cps | Hot paste final visc, cps, 98° C. | Time until tack free, sec | Time until dry hard, sec | Wet film tensile strength, g force | Pot life rating @ 180° F. | Minimum flowable temp, ° F. | Re-softening temp, ° F. |
|---|---|---|---|---|---|---|---|---|
| 1 | 18000 | 1700 | <5 | <10 | 75 | 3.5 | 160 | 150 |
| 2 | 14000 | 2500 | 65 | 100 | * | | | |
| 3 | 13000 | 1150 | 4020 | 5700 | * | | | |
| 4 | | 2300 | <5 | <10 | 108 | 0.5 | >180 | >180 |
| 5 | 13000 | 2400 | <5 | <10 | 65 | 3.0 | 170 | 150 |
| 6 | 16000 | 1500 | <5 | <10 | 50 | 4.0 | 160 | 150 |
| 7 | 11000 | 1300 | <5 | <10 | 75 | 3.5 | 170 | 150 |

*Too weak to test

Example 8

A formulation was prepared having the following composition (on an as-is basis):

16% starch which had been acid-thinned to approximately 600,000 mol wt and substituted with about 4 wt % hydroxypropyl groups (approx. 10% moisture).
2.3% kappa carrageenan (approx. 9% moisture)
26% Sorbitol Special (24% moisture)
6.7% glycerine (1% moisture)
49% added water When the moisture in the components is taken into account, the total solids of the composition was 44%. The starch to carrageenan ratio was 6.75/1, and the ratio of plasticizer to thickener (starch plus carrageenan) was 1.6/1. The plasticizer was composed of 75% Sorbitol Special and 25% glycerine. The components were mixed together and then heated to 98° C. for 15 minutes (or to 92° C. for 30 minutes), then poured hot onto a surface and drawn down into a film.

To control the temperature of the surface onto which films were cast, a stream of water was passed underneath and in contact with that surface. In this experiment, the water stream heated water, rather than chilled water as in the previous examples. The surface temperature was controlled by adjusting the thermostat in the water reservoir—a conventional recirculating water bath.

To determine "minimum flow temperature" and "gel temperature", masses were cooked in an RVA, then transan open draw and other rigors of capsule production.) At higher temperatures, the film thicknesses were lower (probably due to flow on the heated surface). When the film strengths were normalized to film thickness (g force per mm thickness), the temperature effect was especially dramatic—increasing 5 fold as the surface temperature increased from 53° F. to 150° F. The "as-is" film strength, uncorrected for film thickness, increased 4 fold.

Film rates were not quantified, but all conditions generated films which could be lifted and handled in under a minute.

Without being bound by theory, it is possible that the higher film strength observed when the surface temperature was higher is due to larger, greater numbers and/or more perfect helices. When the films cool slowly, they have time and mobility near the gelation temperature to form larger and/or more perfect helices. A higher percentage of the carrageenan may be involved in helices compared to material that is quench-cooled.

Example 9

Experiments were performed using compositions like that of Example 8, but in which the carrageenan content was reduced by 25% and the total mass solids percentage was increased. These compositions had a mass viscosity and wet film strength similar to that exhibited by the formulation of Example 8. The composition and properties of the two soft gels are compared in Table 2 below. The two gel masses have similar viscosity/temperature profiles, and gel at similar temperatures. (As mentioned above, a flow rating of 5 is similar to water. A rating of zero indicates that the sample is gelled and there is no flow. A rating of at least 3 is preferred for handing on commercial equipment.)

TABLE 2

| mass solids, % | % carrageenan | % starch | Flow rateing 180 F | Flow rating 170 F | Flow rating 160 F | Flow rating 150 F | Breaking strength, g 53 F filming | Breaking strength, g 105 F filming |
|---|---|---|---|---|---|---|---|---|
| 44 | 4.1 | 37 | 4.5 | 4.0 | 2.0 | 0.0 | 57 | 180 |
| 48 | 5.2 | 42 | 4.0 | 3.0 | 2.0 | 0.0 | — | 78 |

A 25% reduction in carrageenan makes the composition significantly less costly. Increased mass solids percentage reduces shrinkage and drying costs.

Example 10

Starch-based compositions were prepared containing the same ingredients as in Example 8, except iota carrageenan was used as a complete replacement for kappa carrageenan. However, films formed from such compositions had a slow film formation rate. In addition, the films formed were soft, weak, and very elastic.

Tests were then performed using a composition like that of Example 8, except that it included a combination of kappa and iota carrageenan, rather than only kappa carrageenan. This change resulted in stronger films (higher yield stress) than either of the two types of carrageenan alone. The strongest films comprised a 50/50 (weight) combination of the two. As much as 50% increase in film strength was measured with the 50/50 blend of kappa/iota compared with the kappa-only films.

The temperature at which the kappa-only gel mass became a rigid gel was high—about 160° F. for the composition of Example 8 at 44% solids. The mass viscosity builds rapidly as its temperature is dropped below 180° F. This could be a problem in manufacturing operations, because the hot mass could set up in a location in manufacturing equipment that is inadvertently underheated. Further, even higher temperatures (190° F. plus) are needed to re-soften the kappa-only gel for capsule sealing. Moreover, kappa carrageenan has a very sharp liquid-gel transition, whereas iota's transition is rather broad.

Because the strength of films formed from kappa/iota blends were not a mathematical combination of the two individual carrageenans, and a 50/50 combination of the two gave the strongest films, a mixed gel structure was strongly implied. Carrageenan gels by coiling portions of its carbohydrate backbone into helixes with portions of another carrageenan molecule. If the gel is composed of helixes containing one strand of kappa carrageenan and one strand of iota carrageenan, predicting the softening temperature is not straightforward.

We therefore prepared gel masses composed of either kappa carrageenan, or a 50/50 blend of kappa and iota. All other aspects of the formula were held constant (see Example 8 for the formulation details). A series of gel masses with varying total solids were prepared for each carrageenan composition. The effects on gel temperature are illustrated in Table 3 below. ("Minimum flow" and "gel temperature" are as defined above.)

TABLE 3

Effect of carrageenan on mass flow properties and gel temperature

| | approx min. flow temp, deg F. | | approx gel temp, deg F. | |
|---|---|---|---|---|
| % ds | kappa | kappa/iota | kappa | kappa/iota |
| 42 | 160 | 150 | 150 | 140 |
| 44 | 165 | 160 | 160 | 150 |
| 45 | 170 | 160 | 160 | 150 |
| 46 | 180 | 170 | 160 | 150 |
| 47 | 185 | 170 | 160 | 150 |

It can be seen that replacing half of the kappa carrageenan with iota decreased the temperature at which the mass will flow, and decreased its gel temperature, by about 10° F. for each of the solids levels tested.

Figure 2:
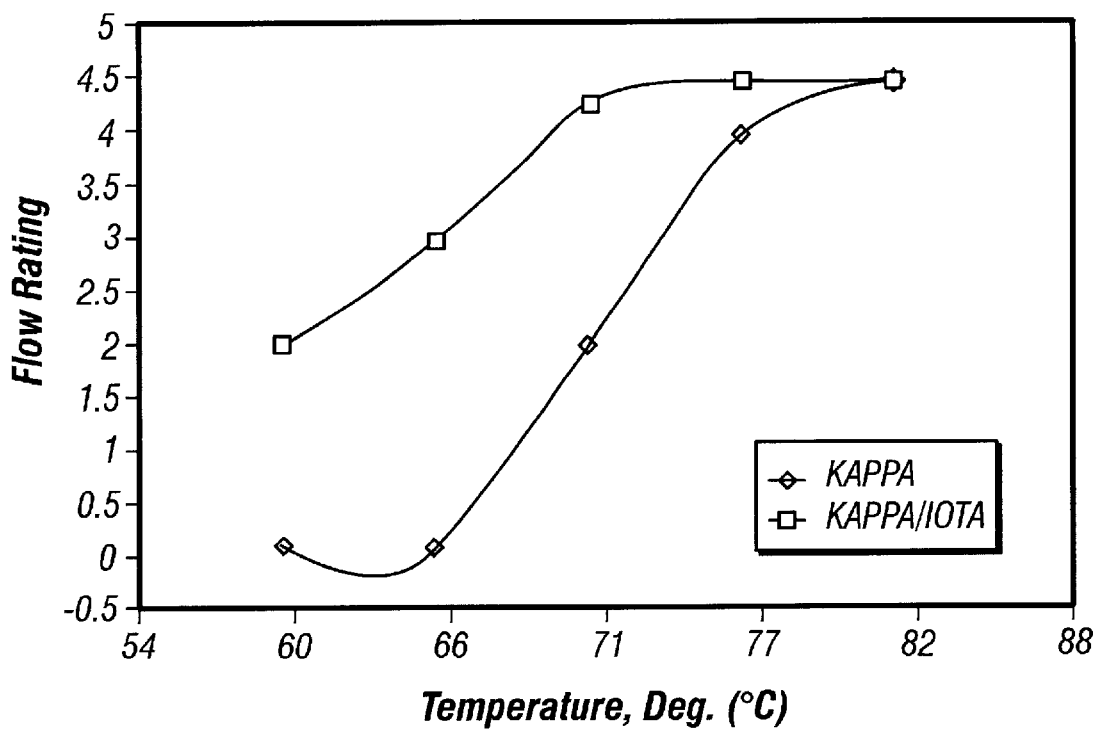
FIG. 2 is a graph showing the effect of temperature on flow and gelation for compositions containing different types of carrageenan.

At 180° F. the two formulations had similar flow properties, but the kappa-only samples thickened rapidly with drop in temperature. FIG. 2 illustrates the effect. Lower gel temperature, and more gradual gelation, should make the films made from kappa/iota mixtures easier to handle and easier to seal.

Figure 3:
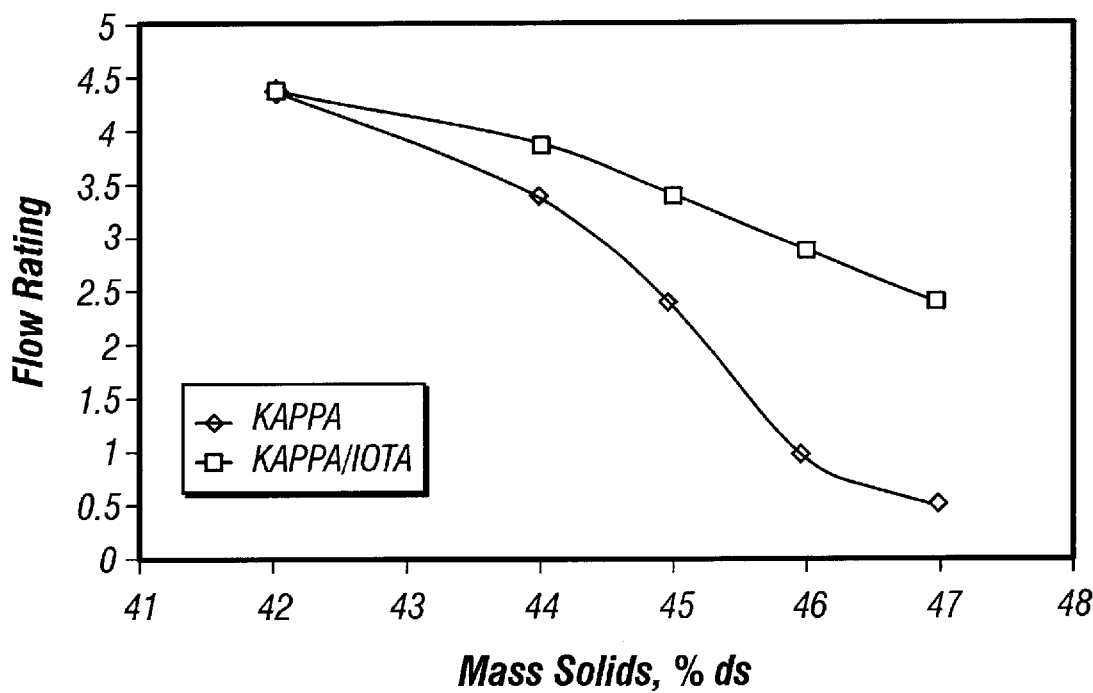
FIG. 3 is a graph showing the effect of mass solids percentage on the flowability of compositions containing different types of carrageenan.

Table 3 above illustrates the importance of solids control during handling of these formulations. FIG. 3 illustrates the rapid decrease in mass flowability at 170° F. as mass solids increases. The effect is especially pronounced for the kappa-only formulation. Blending iota carrageenan with kappa allows for higher solids while maintaining manageable viscosity.

Example 11

Two films that comprised the same ingredients as Example 10 were dipped in mineral oil and then were re-melted and sealed together. During capsule production, gelatin films are typically coated with oil before they are sealed. Without being bound by theory, it is believed that in the absence of the oil coating, evaporative cooling makes it difficult to seal the films (the rapid evaporation cools the films below their gel point by the time the two surfaces came together). The mineral oil appeared to suppress evaporation and the starch-based films could be readily sealed. Both films made with kappa carrageenan and with kappa/iota blends sealed readily using this technique.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A film-forming composition, comprising: starch material having an average molecular weight of about 100,000–2,000,000 and a
dextrose equivalent less than about 1 and selected from the group consisting of (a)
starch which has been chemically modified with a monoreactive moiety to a
degree of substitution of least about 0.015 and is selected from the group
consisting of ether and ester derivatives of starch and (b) waxy starch; gum comprising a combination of kappa carrageenan and iota carrageenan; and plasticizer comprising at least one polyol; wherein the composition is gelatin-free, and wherein the dry solids in the composition
comprise 25–75% starch material, 25–75% plasticizer, and 0.1–15% gum.

2. The composition of claim 1, further comprising water.

3. The composition of claim 2, wherein the composition comprises 30–70% by weight dry solids.

4. The composition of claim 1, wherein the weight ratio of gum to starch is from about 0.1:1 to about 1:1.

5. The composition of claim 1, wherein the weight ratio of starch and gum to plasticizer is from about 1:0.8 to about 1:3.

6. The composition of claim 1, wherein the starch material is selected from the group consisting of hydroxypropyl, hydroxyethyl, succinate, and octenyl succinate starch.

7. The composition of claim 1, wherein the starch material comprises hydroxypropylated potato starch having a degree of substitution of about 0.015–0.30 and a molecular weight of about 100,000–2,000,000.

8. The composition of claim 1, wherein the gum further comprises at least one material that is selected from the group consisting of locust bean, xanthan, gellan, agar, alginates, guar, gum arabic, and pectin.

9. The composition of claim 1, wherein the weight ratio of kappa carrageenan to iota carrageenan is about 1:1.

10. The composition of claim 1, wherein the plasticizer is selected from the group consisting of glycerol, sorbitol, maltitol, and mixtures thereof.

11. The composition of claim 1, further comprising at least one monovalent or divalent cation.

12. The composition of claim 11, wherein the cation is selected from the group consisting of sodium, potassium, and calcium, and mixtures thereof.

13. The composition of claim 1, wherein:
the starch material is selected from the group consisting of ether and ester derivatives of starch having a degree of substitution of about 0.015–0.30.

14. An edible film comprising the composition of any of claims 1–12.

15. A soft gel capsule comprising a sealed capsule wall and a first substance that is
encapsulated by the sealed capsule wall;
wherein the capsule wall comprises a composition according to any of claims 1–12.

16. The capsule of claim 15, wherein the capsule wall consists essentially of a said composition.

17. The capsule of claim 15, wherein the first substance is edible.

18. The capsule of claim 15, wherein the first substance is selected from the group consisting of drugs, vitamins, nutritional supplements, and pre-measured food additives.

19. A method of encapsulating a first substance, comprising the steps of:
providing a first substance and an edible film that comprises a composition according to any of claims 1–12; and
encapsulating the first substance in the film.

20. The method of claim 19, wherein the first substance is selected from the group consisting of drugs, vitamins, nutritional supplements, and pre-measured food additives.

21. The method of claim 19, wherein the film is formed at a temperature of at least about 100° F.

* * * * *